(12) United States Patent
Mueller et al.

(10) Patent No.: US 10,359,334 B2
(45) Date of Patent: Jul. 23, 2019

(54) FLUID LEAKAGE DETECTION FOR A MILLISECOND ANNEAL SYSTEM

(71) Applicant: Mattson Technology, Inc., Fremont, CA (US)

(72) Inventors: Manuel Mueller, Neu-Ulm (DE); Dieter Hezler, Lonsee-Halzhause (DE)

(73) Assignee: Mattson Technology, Inc., Fremont, CA (US)

( * ) Notice: Subject to any disclaimer, the term of this patent is extended or adjusted under 35 U.S.C. 154(b) by 214 days.

(21) Appl. No.: 15/377,217

(22) Filed: Dec. 13, 2016

(65) Prior Publication Data

US 2017/0191897 A1 Jul. 6, 2017

Related U.S. Application Data

(60) Provisional application No. 62/272,849, filed on Dec. 30, 2015.

(51) Int. Cl.
*G01M 3/20* (2006.01)
*G01N 33/00* (2006.01)
*H01L 21/67* (2006.01)

(52) U.S. Cl.
CPC .......... *G01M 3/20* (2013.01); *G01N 33/0036* (2013.01); *H01L 21/6719* (2013.01); *H01L 21/67288* (2013.01)

(58) Field of Classification Search
CPC ................. G01M 3/20; H01L 21/6719; H01L 21/67288; G01N 33/0036
USPC ......................................................... 73/40.7
See application file for complete search history.

(56) References Cited

U.S. PATENT DOCUMENTS

| 6,204,203 B1 | 3/2001 | Narwankar et al. |
| 7,442,415 B2 | 10/2008 | Conley, Jr. et al. |
| 7,790,633 B1 | 9/2010 | Tarafdar et al. |
| 8,323,754 B2 | 12/2012 | Olsen et al. |
| 8,809,175 B2 | 8/2014 | Tsai et al. |
| 9,093,468 B2 | 7/2015 | Tsai et al. |
| 2001/0014372 A1 | 8/2001 | Katano et al. |
| 2002/0014084 A1* | 2/2002 | Kaneda ............ H01L 21/67248 62/176.6 |

(Continued)

FOREIGN PATENT DOCUMENTS

| KR | 2011-0053817 | 5/2011 |
| KR | 2011-0103830 | 9/2011 |

OTHER PUBLICATIONS

PCT International Search Report for corresponding PCT Application No. PCT/US2016/066344, dated Apr. 10, 2017, 3 pages.

(Continued)

*Primary Examiner* — Nathaniel T Woodward
(74) *Attorney, Agent, or Firm* — Dority & Manning, P.A.

(57) ABSTRACT

Systems and methods for detecting a fluid leak associated with fluid cooled components in a millisecond anneal system are provided. In one example implementation, a millisecond anneal system can include a processing chamber having one or more fluid cooled components. The system can include a gas flow system configured to provide for the flow of process gas in the processing chamber. The system can include a vapor sensor configured to measure vapor in process gas flowing through the gas flow system for detecting a fluid leak associated with the one or more fluid cooled components.

17 Claims, 12 Drawing Sheets

(56) References Cited

U.S. PATENT DOCUMENTS

| | | | |
|---|---|---|---|
| 2012/0090383 A1* | 4/2012 | Lopez | G01M 3/228 73/40.7 |
| 2014/0273419 A1* | 9/2014 | Ranish | H01L 21/67115 438/507 |
| 2015/0140838 A1 | 5/2015 | Kashefi et al. | |
| 2015/0170938 A1 | 6/2015 | Seigeot | |

OTHER PUBLICATIONS

PCT International Preliminary Report on Patentability for corresponding PCT Application No. PCT/US2016/066344, dated Jul. 12, 2018—12 pages.

Ragnarsson et al., "The Importance of Moisture Control for EOT Scaling of Hf-Based Dielectrics," *Journal of the Electrochemical Society*, vol. 156, Issue 6, Apr. 3, 2009, pp. H416-H423.

Ferrari et al., "Diffusion Reaction of Oxygen in HfO2/SiO2/Si Stacks," *The Journal of Physical Chemistry B*, vol. 110, No. 30, Jul. 12, 2006, pp. 14905-14910.

Driemeier et al., "Thermochemical behavior of hydrogen in hafnium silicate films on Si," Applied Physics Letters, vol. 89, Issue 5, Aug. 2006,—4 pages.

Driemeier et al., "Room temperature interactions of water vapor with Hf O2 films on Si," Applied Physics Letters, vol. 88, Issue 20, May 2006—3 pages.

Conley, Jr. et al., "Densification and improved electrical properties of pulse-deposited films via in situ modulated temperature annealing," *Applied Physics Letters*, vol. 84, Issue 11, Mar. 15, 2004, pp. 1913-1915.

Nakajima et al., "Experimental Demonstration of Higher-k phase HfO2 through Non-equilibrium Thermal Treatment," ECS Transactions 28.2 (2010), pp. 203-212.

Wu et al., "Device Performance and Reliability Improvement for MOSFETs With HfO2 Gate Dielectrics Fabricated Using Multideposition Room-Temperature Multiannealing," IEEE Electron Device Letters, vol. 32, Issue 9, Sep. 2011, pp. 1173-1175.

\* cited by examiner

FLUID LEAKAGE DETECTION FOR A MILLISECOND ANNEAL SYSTEM

PRIORITY CLAIM

The present application claims the benefit of priority of U.S. Provisional Application Ser. No. 62/272,849, filed Dec. 30, 2015, entitled "Water Leakage Detection for Millisecond Anneal System," which is incorporated herein by reference.

FIELD

The present disclosure relates generally to thermal processing chambers and more particularly to millisecond anneal thermal processing chambers used for processing of substrates, such as semiconductor substrates.

BACKGROUND

Millisecond anneal systems can be used for semiconductor processing for the ultra-fast heat treatment of substrates, such as silicon wafers. In semiconductor processing, fast heat treatment can be used as an anneal step to repair implant damage, improve the quality of deposited layers, improve the quality of layer interfaces, to activate dopants, and to achieve other purposes, while at the same time controlling the diffusion of dopant species.

Millisecond, or ultra-fast, temperature treatment of semiconductor substrates can be achieved using an intense and brief exposure of light to heat the entire top surface of the substrate at rates that can exceed $10^{4°}$ C. per second. The rapid heating of just one surface of the substrate can produce a large temperature gradient through the thickness of the substrate, while the bulk of the substrate maintains the temperature before the light exposure. The bulk of the substrate therefore acts as a heat sink resulting in fast cooling rates of the top surface.

SUMMARY

Aspects and advantages of embodiments of the present disclosure will be set forth in part in the following description, or may be learned from the description, or may be learned through practice of the embodiments.

One example aspect of the present disclosure is directed to a thermal processing system. The system can include a processing chamber having one or more fluid cooled components. The system can include a gas flow system configured to provide for the flow of process gas in the processing chamber. The system can include a vapor sensor configured to measure vapor in process gas flowing through the gas flow system for detecting a fluid leak associated with the one or more fluid cooled components.

Another example aspect of the present disclosure is directed to a method for detecting a fluid leak in a millisecond anneal system. The method includes obtaining, by one or more processor circuits, one or more signals from a humidity sensor configured to measure humidity in process gas flowing through a gas flow system. The gas flow system can be configured to provide for the flow of process gas in a processing chamber having one or more fluid cooled components. The method can include detecting, by the one or more processor circuits, a fluid leak associated with the one or more fluid cooled components in the processing chamber based at least in part on the one or more signals from the humidity sensor.

Variations and modification can be made to the example aspects of the present disclosure. Other example aspects of the present disclosure are directed to systems, methods, devices, and processes for thermally treating a semiconductor substrate.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
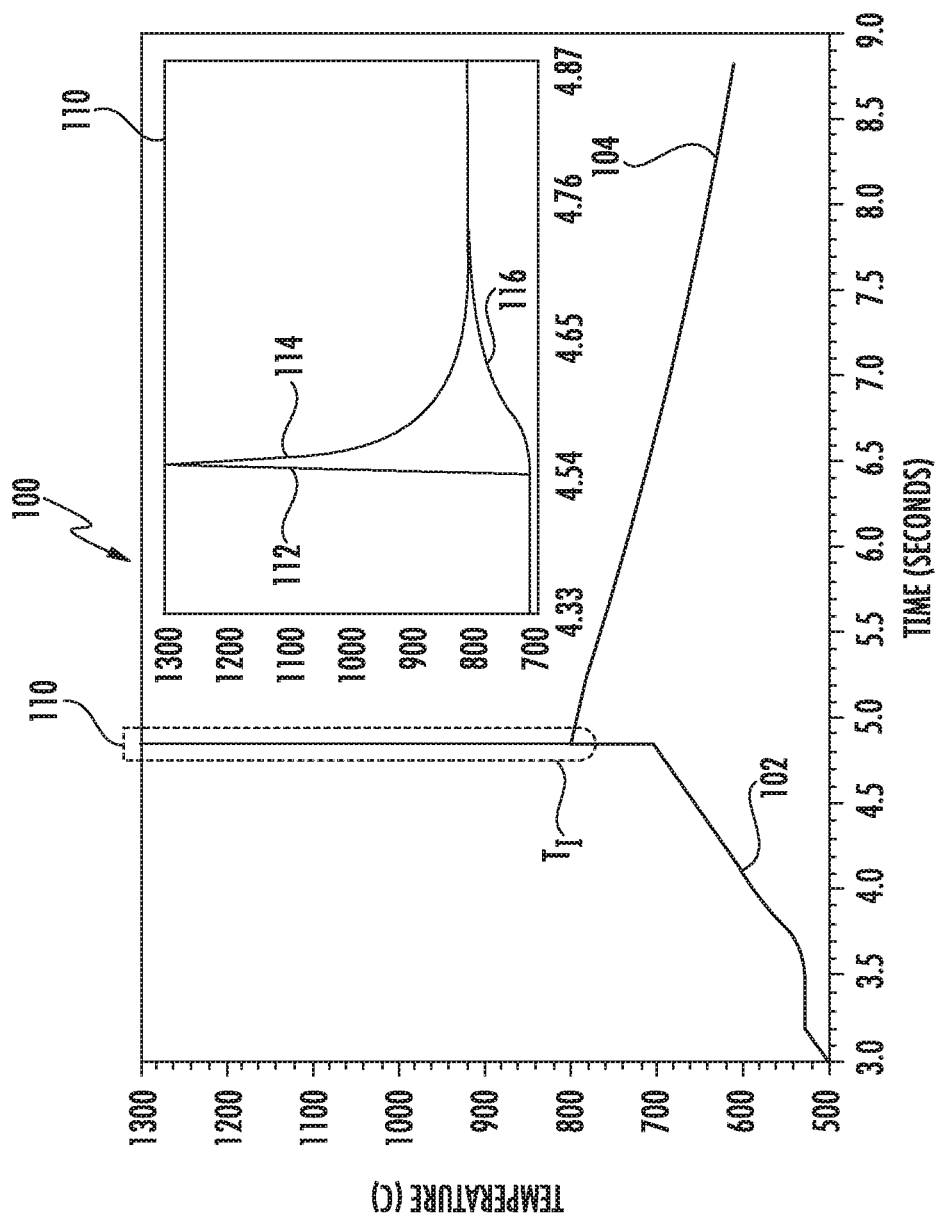
FIG. 1 depicts an example millisecond anneal heating profile according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Overview

Example aspects of the present disclosure are directed to detecting fluid leaks in fluid cooled components of a millisecond anneal system. Aspects of the present disclosure are discussed with reference to a "wafer" or semiconductor wafer for purposes of illustration and discussion. Those of ordinary skill in the art, using the disclosures provided herein, will understand that the example aspects of the present disclosure can be used in association with any semiconductor substrate or other suitable substrate. In addition, the use of the term "about" in conjunction with a numerical value refers to within 10% of the stated numerical value.

In addition, aspects of the present disclosure are discussed with reference to a millisecond anneal system for purposes of illustration and discussion. Those of ordinary skill in the art, using the disclosures provided herein, will understand that example aspects of the present disclosure can be used with other suitable thermal processing systems.

Millisecond, or ultra-fast, thermal treatment of semiconductor wafers can be achieved using an intense and brief exposure of light to heat the entire top surface of the wafer at rates that can exceed $10^{4°}$ C./sec. The flash of light can be applied to a semiconductor substrate, which was previously heated to an intermediate temperature $T_i$ at ramp rates of, for instance, up to 150° C./sec. This slower heating process to $T_i$ can be accomplished by continuous mode arc lamps located on the bottom side of the chamber. These lamps heat the entire bulk of the wafer through the bottom surface of the wafer.

As discussed in more detail below, the process chamber of an example millisecond anneal system can be divided by a wafer plane plate into two sub-chambers, a top chamber and a bottom chamber. The wafer plane plate can be a fluid cooled (e.g., water cooled) aluminum frame which acts as holder for the wafer support plate. The walls of each of the sub-chambers can include reflector mirrors on four sides, sealed against the chamber frame. These reflectors can be fluid cooled (e.g., water cooled) by internal fluid channels. The top and bottom wall of the sub-chambers can include water cooled quartz windows transparent to the light of the heating source, which are again sealed against the chamber frame. Each reflector mirror can have its own water inlet and outlet connection. In some embodiments, the fluid cooling system (e.g., water cooling system) can be such that the bottom chamber parts, the top chamber parts, and the wafer plane plate are connected in parallel, whereas the four reflector mirrors of each sub-chamber are connected in series. In some embodiments, the water window can have its own closed loop water circuit separate from the other chamber parts. An example closed loop fluid cooling system in a millisecond anneal system according to example embodiments of the present disclosure will be discussed in more detail with reference to FIG. 14.

The process chamber can be located inside a process module, which can have a fluid leak detection system on the bottom floor of the process module. This leak detection system is able to detect fluid leaks, which are external to the process chamber, (e.g., leaking water connectors, leaks on the outside of the chamber parts, etc.). The leak detection system can use the resistivity change of a sensor material when wetted by water. This type of leak detection system cannot be used inside the chamber due to the hostile environment (e.g., high amount of UV light radiation). Also it does not meet the cleanliness requirements of the thermal treatment process.

For this reason, fluid (e.g., water) leaking into the processing chamber cannot be detected directly and immediately. As the chamber is leak tight, fluid leaking into the chamber, will collect on the bottom water window. Eventually the leak will be detected during the regular maintenance inspection. As the main failure mechanism is corrosion of aluminium or erosion of rubber gaskets, it may be that only small-sized leaks can develop in-between maintenance inspections The heat treatment in a millisecond anneal system is preferably carried out in a controlled, clean process gas ambient at atmospheric pressure. The ambient can be pure nitrogen. In some cases gases such as oxygen, ammonia, hydrogen, or forming gas, or mixtures thereof, are also used. In terms of the process gas ambient, the chamber can be an open flow system. Process gas can be constantly entering the chamber through the gas inlets located, for instance, in the four corners of the top chamber and exiting through the gas outlets located in the four corners of the bottom chamber. Even small fluid leaks can contaminate the process gas ambient by evaporation of water and water impurities, resulting in errors in the processing of the semiconductor substrate. Depending on leak size, a large number of semiconductor substrates can processed in error before the leak is eventually detected by an external sensor. In the case of very small leaks, the leak might not be detected at all.

According to example embodiments of the present disclosure, water or other fluid leaking into the process chamber can be detected by a sensor measuring the amount of vapor (e.g., humidity) in the gas vented from the chamber. In this way, leaks inside the process chamber can be detected between in-maintenance inspections.

For instance, one example embodiment of the present disclosure is directed to a thermal processing system. The thermal processing system includes a processing chamber having one or more fluid cooled components. The thermal processing system includes a gas flow system configured to provide for the flow of process gas in the processing chamber. The thermal processing system includes a vapor sensor (e.g., a humidity sensor) configured to measure vapor (e.g., humidity) in process gas flowing through the gas flow system for detecting a fluid leak (e.g., a water leak) associated with the one or more fluid cooled components. As used herein a "water leak" refers to a leak of any fluid that includes water or mixture containing water.

In some embodiments, the gas flow system can include one or more exhaust vent openings in the processing chamber to exhaust process gas from the processing chamber. The vapor sensor can be configured to measure vapor in process gas flowing downstream of the exhaust vent openings in the gas flow system. In some embodiments, the processing chamber can include a wafer plane plate dividing the processing chamber into a top chamber and a bottom chamber. The exhaust vent openings can be located in the bottom chamber.

In some embodiments, the gas flow system includes a downstream line coupled to each of the one or more exhaust vent openings. In some embodiments, the vapor sensor can be configured to measure vapor in process gas flowing in the downstream line. In some embodiments, the vapor sensor can be configured to measure vapor in process gas flowing in a bypass line coupled to the downstream line. The gas flow system can include a valve configured to control the flow of gas into the bypass line.

In some embodiments, the system can further include at least on processor circuit. The at least one processor circuit can be configured to obtain signals from the vapor sensor indicative of the vapor in process gas flowing through the gas flow system; and detect the fluid leak associated with the one or more fluid cooled components based at least in part on the signals from the vapor sensor. In some embodiments, the processor circuit can be configured to detect the fluid leak associated with the one or more fluid cooled components at least in part by comparing the amount of vapor in process gas flowing through the gas flow system to a threshold and detecting the fluid leak when the amount of vapor in process gas exceeds the threshold. The processor circuit can be configured to provide an indicator associated with the fluid leak.

In some embodiments, the fluid cooled component can be a wafer plane plate. In some embodiments, the fluid cooled component can be a reflective mirror. In some embodiments, the fluid cooled component can be a water window.

Another example embodiment of the present disclosure is directed to a method for detecting a fluid leak in a millisecond anneal system. The method includes obtaining, by one or more processor circuits, one or more signals from a humidity sensor configured to measure humidity in process gas flowing through a gas flow system. The gas flow system can be configured to provide for the flow of process gas in a processing chamber having one or more fluid cooled components. The method can include detecting, by the one or more processor circuits, a fluid leak associated with the one or more fluid cooled components in the processing chamber based at least in part on the one or more signals from the humidity sensor.

In some embodiments, detecting, by the one or more processors circuits, a fluid leak associated with the one or more fluid cooled components in the processing chamber can include: comparing, by the one or more processor circuits, the humidity in the process gas to a threshold; and detecting, by the one or more processor circuits, the fluid leak when the humidity in the process gas exceeds the threshold. In some embodiments, the method further comprises providing an indicator associated with the fluid leak. In some embodiments, the humidity sensor is configured to measure humidity in process gas flowing downstream of one or more exhaust vent openings in the processing chamber.

Another example embodiment of the present disclosure is directed to a millisecond anneal system. The millisecond anneal system includes a processing chamber having a wafer plane plate dividing the processing chamber into a top chamber and a bottom chamber, the processing chamber having one or more reflective mirrors. The system includes a gas flow system configured to provide for the flow of process gas in the processing chamber. The gas flow system can include at least one vent opening in the top chamber for providing process gas to the processing chamber and at least one exhaust vent opening in the bottom chamber for exhausting process gas from the processing chamber. The gas flow system further can include a downstream line coupled to the at least one exhaust vent opening. The system can include a fluid cooling system configured to circulate fluid through one or more of the wafer plane plate and the one or more reflective mirrors. The system can include a humidity sensor configured to measure humidity in process gas flowing through the downstream line for detecting a leak associated with the fluid cooling system.

In some embodiments, the system can include a processor circuit. The processor circuit can be configured to perform operations. The operations can include obtaining signals from the humidity sensor indicative of the humidity in process gas flowing through the downstream line; and detecting the leak associated with the fluid cooling system based at least in part on the signals from the humidity sensor.

Example Millisecond Anneal Systems

An example millisecond anneal system can be configured to provide an intense and brief exposure of light to heat the top surface of a wafer at rates that can exceed, for instance, about $10^{4°}$ C./s. FIG. 1 depicts an example temperature profile 100 of a semiconductor substrate achieved using a millisecond anneal system. As shown in FIG. 1, the bulk of the semiconductor substrate (e.g., a silicon wafer) is heated to an intermediate temperature $T_i$ during a ramp phase 102. The intermediate temperature can be in the range of about 450° C. to about 900° C. When the intermediate temperature $T_i$ is reached, the top side of the semiconductor substrate can be exposed to a very short, intense flash of light resulting in heating rates of up to about $10^{4°}$ C./s. Window 110 illustrates the temperature profile of the semiconductor substrate during the short, intense flash of light. Curve 112 represents the rapid heating of the top surface of the semiconductor substrate during the flash exposure. Curve 116 depicts the temperature of the remainder or bulk of the semiconductor substrate during the flash exposure. Curve 114 represents the rapid cool down by conductive of cooling of the top surface of the semiconductor substrate by the bulk of the semiconductor substrate acting as a heat sink. The bulk of the semiconductor substrate acts as a heat sink generating high top side cooling rates for the substrate. Curve 104 represents the slow cool down of the bulk of the semiconductor substrate by thermal radiation and convection, with a process gas as a cooling agent.

An example millisecond anneal system can include a plurality of arc lamps (e.g., four Argon arc lamps) as light sources for intense millisecond long exposure of the top surface of the semiconductor substrate—the so called "flash." The flash can be applied to the semiconductor substrate when the substrate has been heated to an intermediate temperature (e.g., about 450° C. to about 900° C.). A plurality of continuous mode arc lamps (e.g., two Argon arc lamps) can be used to heat the semiconductor substrate to the intermediate temperature. In some embodiments, the heating of the semiconductor substrate to the intermediate temperature is accomplished through the bottom surface of the semiconductor substrate at a ramp rate which heats the entire bulk of the wafer.

Figure 2:
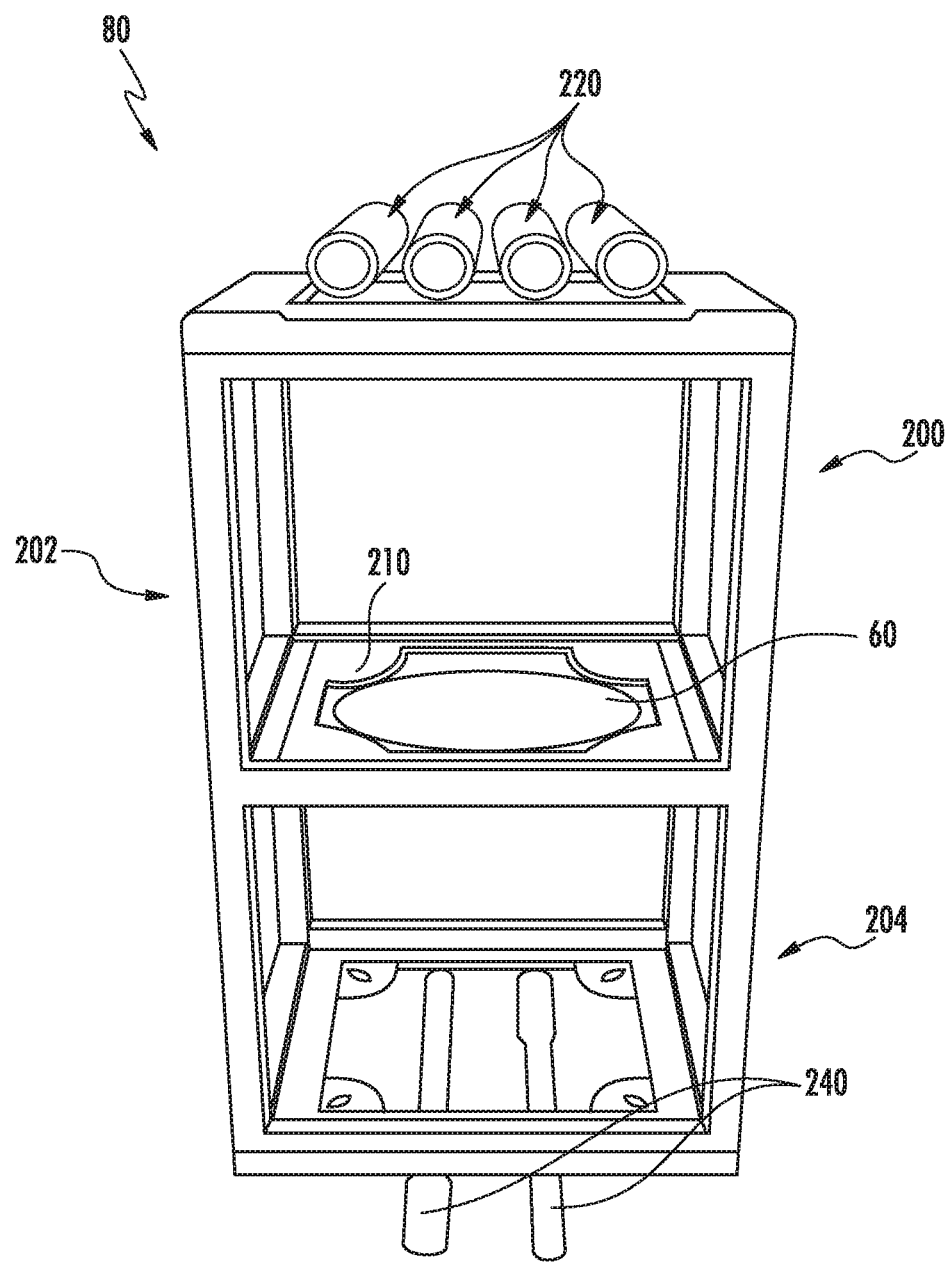
FIG. 2 depicts an example perspective view of a portion of an example millisecond anneal system according to example embodiments of the present disclosure.
Figure 3:
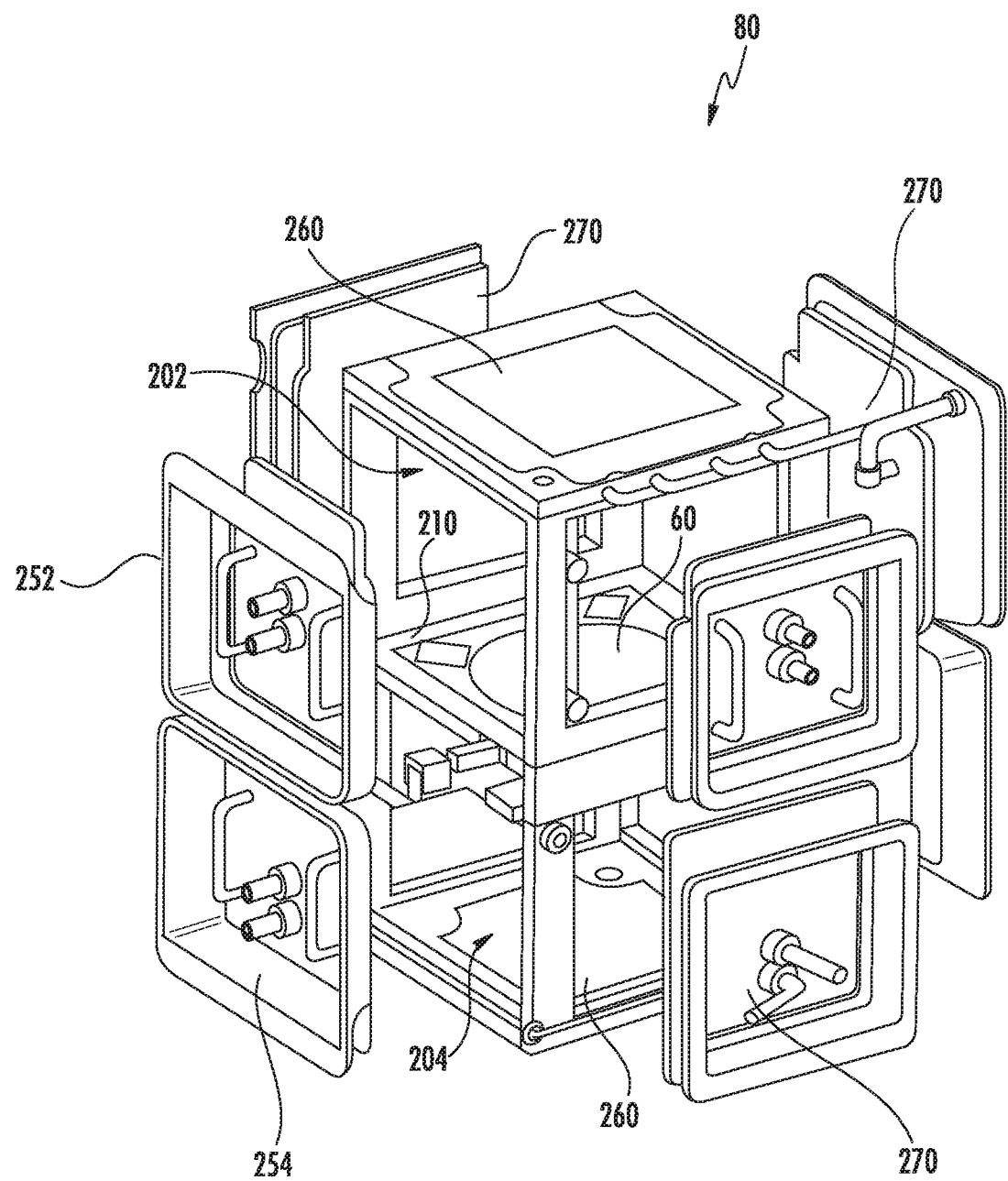
FIG. 3 depicts an exploded view of an example millisecond anneal system according to example embodiments of the present disclosure.
Figure 4:
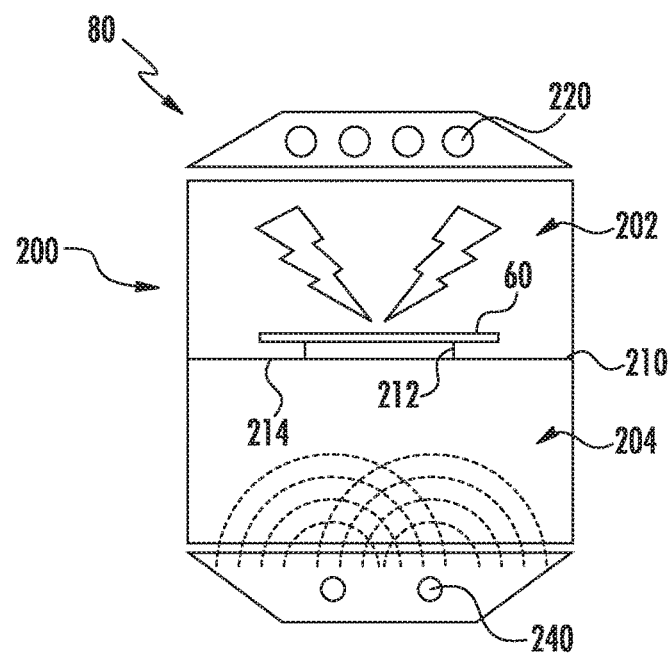
FIG. 4 depicts a cross-sectional view of an example millisecond anneal system according to example embodiments of the present disclosure.

FIGS. 2 to 5 depict various aspects of an example millisecond anneal system 80 according to example embodiments of the present disclosure. As shown in FIGS. 2-4, a millisecond anneal system 80 can include a process chamber 200. The process chamber 200 can be divided by a wafer plane plate 210 into a top chamber 202 and a bottom chamber 204. A semiconductor substrate 60 (e.g., a silicon wafer) can be supported by support pins 212 (e.g., quartz support pins) mounted to a wafer support plate 214 (e.g., quartz glass plate inserted into the wafer plane plate 210).

As shown in FIGS. 2 and 4, the millisecond anneal system 80 can include a plurality of arc lamps 220 (e.g., four Argon arc lamps) arranged proximate the top chamber 202 as light sources for intense millisecond long exposure of the top surface of the semiconductor substrate 60—the so called "flash." The flash can be applied to the semiconductor substrate when the substrate has been heated to an intermediate temperature (e.g., about 450° C. to about 900° C.).

A plurality of continuous mode arc lamps 240 (e.g., two Argon arc lamps) located proximate the bottom chamber 204 can be used to heat the semiconductor substrate 60 to the intermediate temperature. In some embodiments, the heating of the semiconductor substrate 60 to the intermediate temperature is accomplished from the bottom chamber 204 through the bottom surface of the semiconductor substrate at a ramp rate which heats the entire bulk of the semiconductor substrate 60.

As shown in FIG. 3, the light to heat the semiconductor substrate 60 from the bottom arc lamps 240 (e.g., for use in heating the semiconductor substrate to an intermediate temperature) and from the top arc lamps 220 (e.g., for use in providing millisecond heating by flash) can enter the processing chamber 200 through water windows 260 (e.g., water cooled quartz glass windows). In some embodiments, the water windows 260 can include a sandwich of two quartz glass panes between which an about a 4 mm thick layer of water is circulating to cool the quartz panes and to provide an optical filter for wavelengths, for instance, above about 1400 nm.

Figure 5:
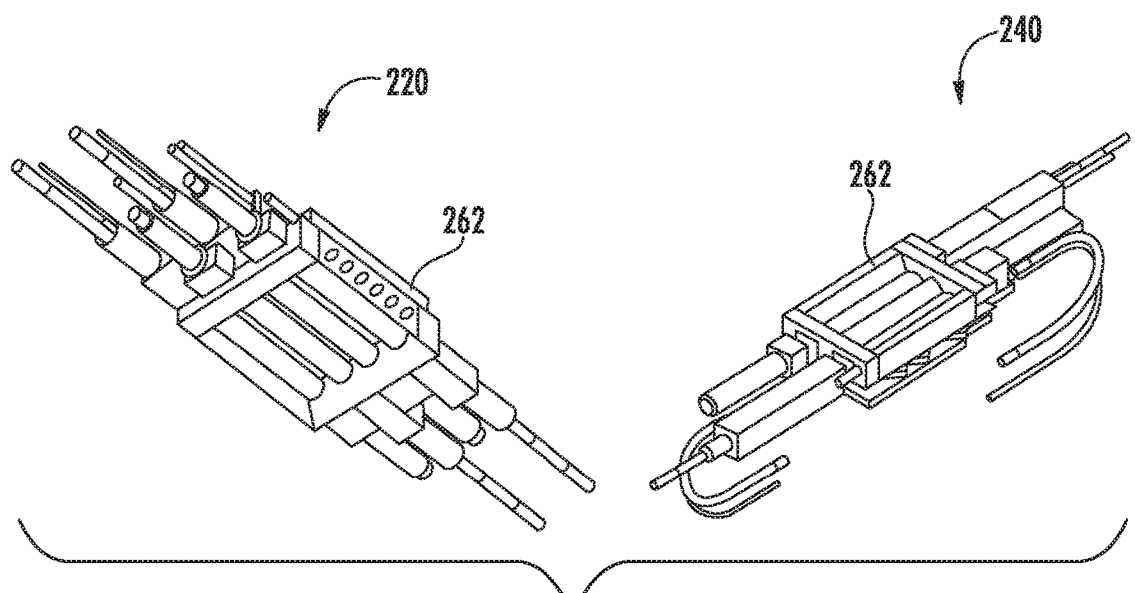
FIG. 5 depicts a perspective view of example lamps used in a millisecond anneal system according to example embodiments of the present disclosure.

As further illustrated in FIG. 3, process chamber walls 250 can include reflective mirrors 270 for reflecting the heating light. The reflective mirrors 270 can be, for instance, water cooled, polished aluminum panels. In some embodiments, the main body of the arc lamps used in the millisecond anneal system can include reflectors for lamp radiation. For instance, FIG. 5 depicts a perspective view of both a top lamp array 220 and a bottom lamp array 240 that can be used in the millisecond anneal system 200. As shown, the main body of each lamp array 220 and 240 can include a reflector 262 for reflecting the heating light. These reflectors 262 can form a part of the reflecting surfaces of the process chamber 200 of the millisecond anneal system 80.

The temperature uniformity of the semiconductor substrate can be controlled by manipulating the light density falling onto different regions of the semiconductor substrate. In some embodiments, uniformity tuning can be accomplished by altering the reflection grade of small size reflectors to the main reflectors and/or by use of edge reflectors mounted on the wafer support plane surrounding the wafer.

Figure 6:
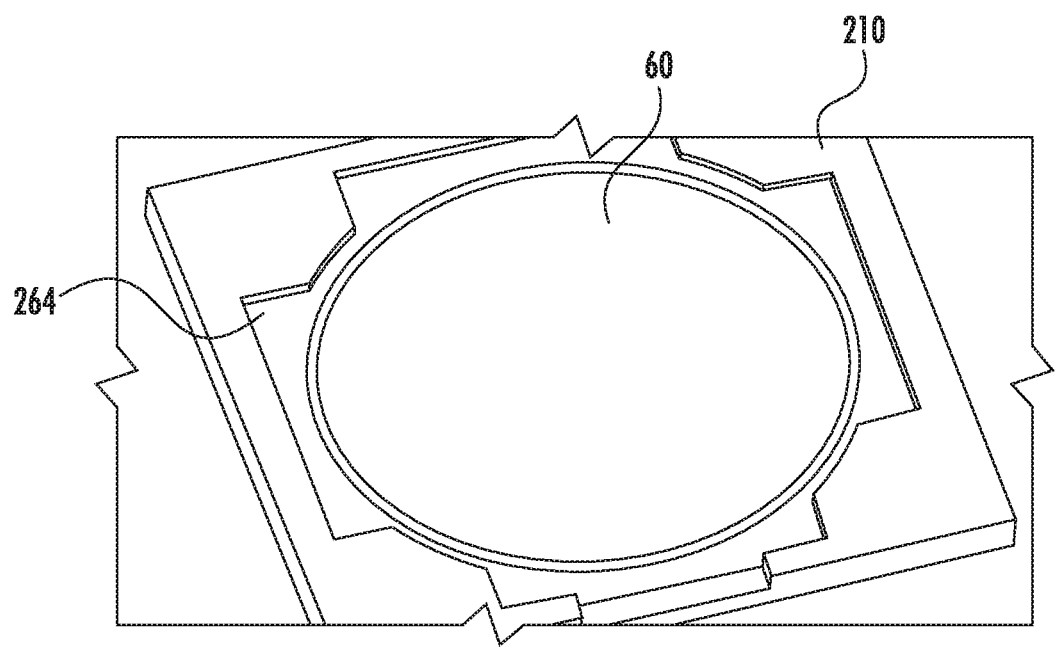
FIG. 6 depicts example edge reflectors used in a wafer plane plate of a millisecond anneal system according to example embodiments of the present disclosure.

For instance, edge reflectors can be used to redirect light from the bottom lamps 240 to an edge of the semiconductor substrate 60. As an example, FIG. 6 depicts example edge reflectors 264 that form a part of the wafer plane plate 210 that can be used to direct light from the bottom lamps 240 to the edge of the semiconductor substrate 60. The edge reflectors 264 can be mounted to the wafer plane plate 210 and can surround or at least partially surround the semiconductor substrate 60.

In some embodiments, additional reflectors can also be mounted on chamber walls near the wafer plane plate 210.

Figure 7:
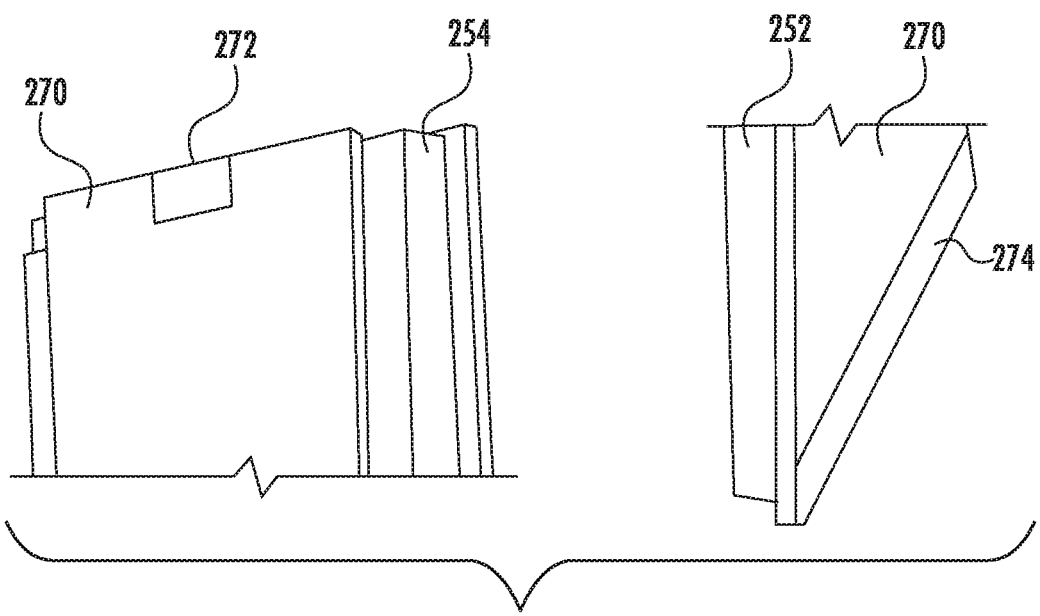
FIG. 7 depicts example reflectors that can be used in a millisecond anneal system according to example embodiments of the present disclosure.

For example, FIG. 7 depicts example reflectors that can be mounted to the process chamber walls that can act as reflector mirrors for the heating light. More particularly, FIG. 7 shows an example wedge reflector 272 mounted to lower chamber wall 254. FIG. 7 also illustrates a reflective element 274 mounted to reflector 270 of an upper chamber wall 252. Uniformity of processing of the semiconductor substrate 60 can be tuned by changing the reflection grade of the wedge reflectors 272 and/or other reflective elements (e.g., reflective element 274) in the processing chamber 200.

Figure 8:
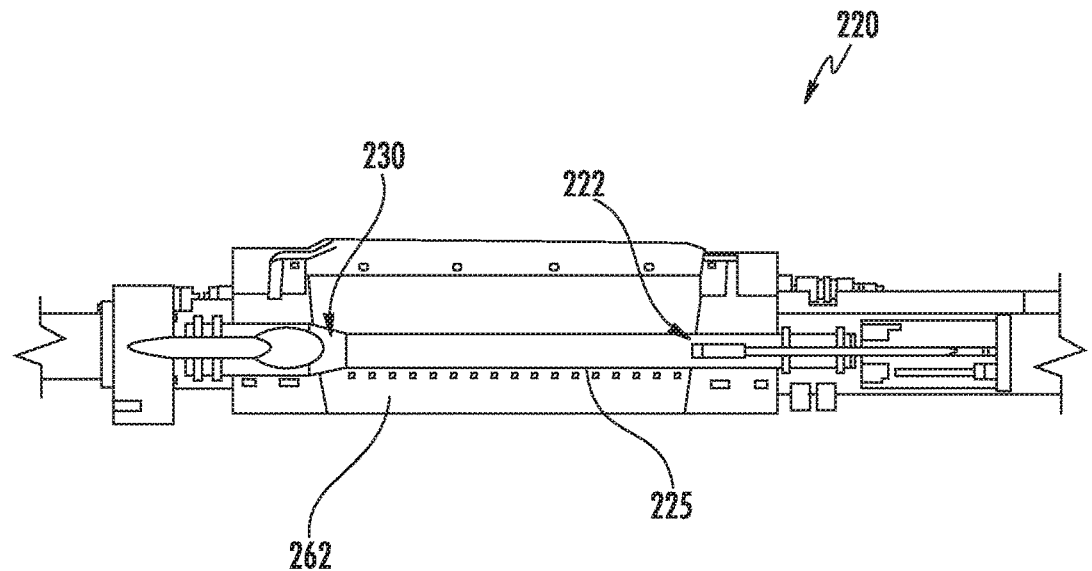
FIG. 8 depicts an example arc lamp that can be used in a millisecond anneal system according to example embodiments of the present disclosure.
Figure 9:
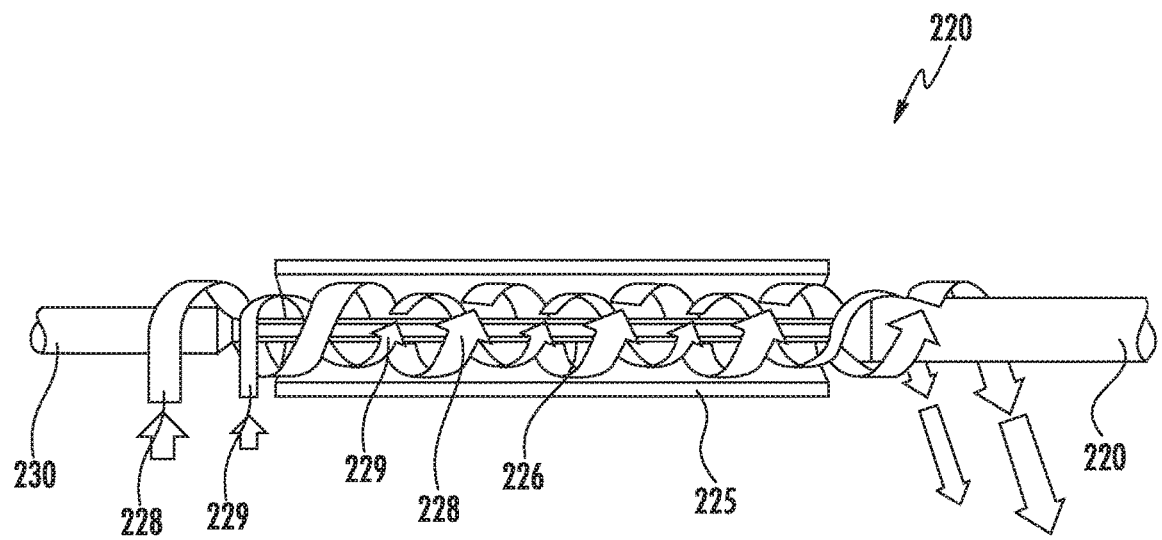
FIGS. 9-10 depict the operation of an example arc lamp according to example embodiments of the present disclosure.

FIGS. 8-11 depict aspects of example upper arc lamps 220 that can be used as light sources for intense millisecond long exposure of the top surface of the semiconductor substrate 60 (e.g., the "flash"). For instance, FIG. 8 depicts a cross-sectional view of an example arc lamp 220. The arc lamp 220 can be, for instance, an open flow arc lamp, where pressurized Argon gas (or other suitable gas) is converted into a high pressure plasma during an arc discharge. The arc discharge takes place in a quartz tube 225 between a negatively charged cathode 222 and a spaced apart positively charged anode 230 (e.g., spaced about 300 mm apart). As soon as the voltage between the cathode 222 and the anode 230 reaches a breakdown voltage of Argon (e.g., about 30 kV) or other suitable gas, a stable, low inductive plasma is formed which emits light in the visible and UV range of the electromagnetic spectrum. As shown in FIG. 9, the lamp can include a lamp reflector 262 that can be used to reflect light provided by the lamp for processing of the semiconductor substrate 60.

Figure 10:
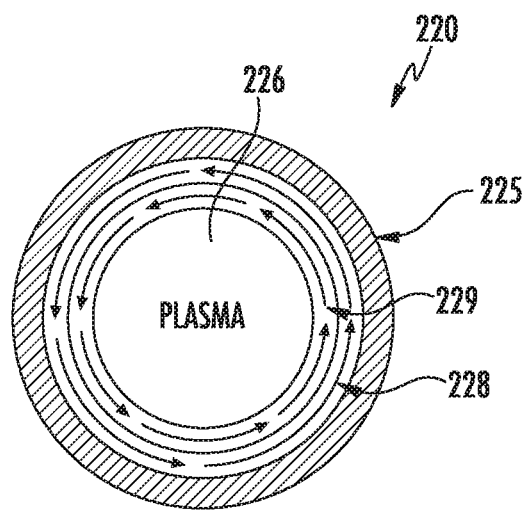
Figure 11:
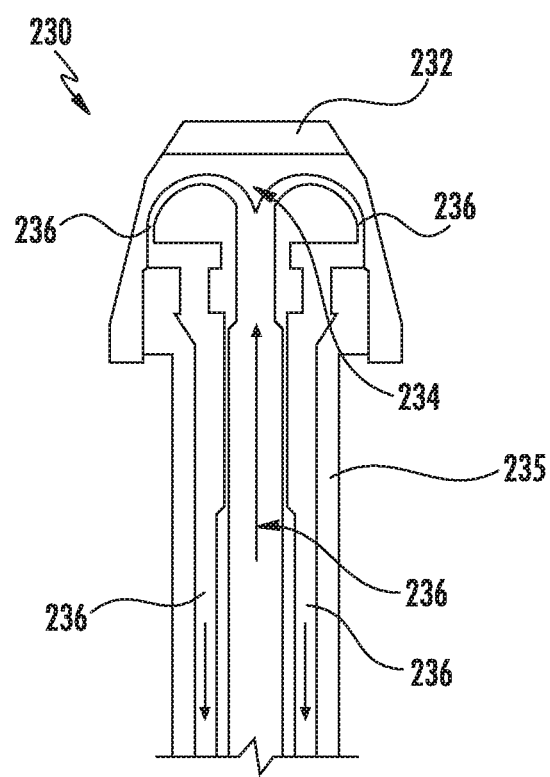
FIG. 11 depicts a cross-sectional view of an example electrode according to example embodiments of the present disclosure.

FIGS. 10 and 11 depict aspects of example operation of an arc lamp 220 in millisecond anneal system 80 according to example embodiments of the present disclosure. More particularly, a plasma 226 is contained within a quartz tube 225 which is water cooled from the inside by a water wall 228. The water wall 228 is injected at high flow rates on the cathode end of the lamp 200 and exhausted at the anode end. The same is true for the Argon gas 229, which is also entering the lamp 220 at the cathode end and exhausted from the anode end. The water forming the water wall 228 is injected perpendicular to the lamp axis such that the centrifugal action generates a water vortex. Hence, along the center line of the lamp a channel is formed for the Argon gas 229. The Argon gas column 229 is rotating in the same direction as the water wall 228. Once a plasma 226 has formed, the water wall 228 is protecting the quartz tube 225 and confining the plasma 226 to the center axis. Only the water wall 228 and the electrodes (cathode 230 and anode 222) are in direct contact with the high energy plasma 226.

FIG. 11 depicts a cross sectional view of an example electrode (e.g., cathode 230) used in conjunction with an arc lamp according to example embodiments of the present disclosure. FIG. 11 depicts a cathode 230. However, a similar construction can be used for the anode 222.

In some embodiments, as the electrodes experience a high heat load, one or more of the electrodes can each include a tip 232. The tip can be made from tungsten. The tip can be coupled to and/or fused to a water cooled copper heat sink 234. The copper heat sink 234 can include at least a portion the internal cooling system of the electrodes (e.g., one or more water cooling channels 236. The electrodes can further include a brass base 235 with water cooling channels 236 to provide for the circulation of water or other fluid and the cooling of the electrodes.

The arc lamps used in example millisecond anneal systems according to aspects of the present disclosure can be an open flow system for water and Argon gas. However, for conservation reasons, both media can be circulated in a close loop system in some embodiments.

Figure 12:
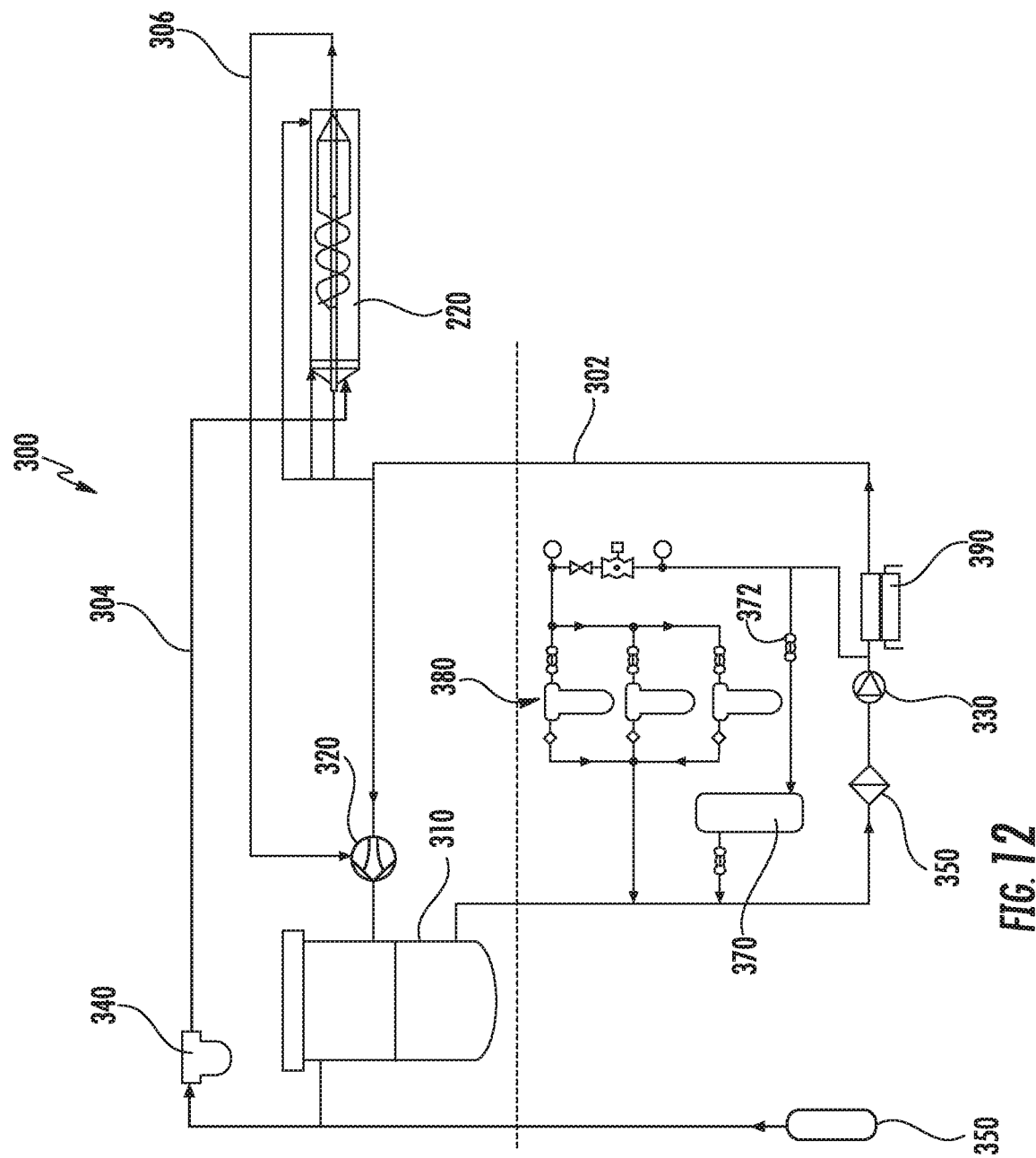
FIG. 12 depicts an example closed loop system for supplying water and gas (e.g., Argon gas) to example arc lamps used in a millisecond anneal system according to example embodiments of the present disclosure.

FIG. 12 depicts an example closed loop system 300 for supplying water and Argon gas needed to operate the open flow Argon arc lamps used in millisecond anneal systems according to example embodiments of the present disclosure.

More particularly, high purity water 302 and Argon 304 is fed to the lamp 220. The high purity water 302 is used for the water wall and the cooling of the electrodes. Leaving the lamp is a gas/water mixture 306. This water/gas mixture 306 is separated into gas free water 302 and dry Argon 304 by separator 310 before it can be re-fed to the inlets of the lamp 220. To generate the required pressure drop across the lamp 220, the gas/water mixture 306 is pumped by means of a water driven jet pump 320.

A high power electric pump 330 supplies the water pressure to drive the water wall in the lamp 220, the cooling water for the lamp electrodes, and the motive flow for the jet pump 320. The separator 310 downstream to the jet pump 320 can be used extracting the liquid and the gaseous phase from the mixture (Argon). Argon is further dried in a coalescing filter 340 before it re-enters the lam 220. Additional Argon can be supplied from Argon source 350 if needed.

The water is passing through one or more particle filters 350 to remove particles sputtered into the water by the arc. Ionic contaminations are removed by ion exchange resins. A portion of water is run through mixed bed ion exchange filters 370. The inlet valve 372 to the ion exchange bypass 370 can be controlled by the water resistivity. If the water resistivity drops below a lower value the valve 372 is opened, when it reaches an upper value the valve 372 is closed. The system can contain an activated carbon filter bypass loop 380 where a portion of the water can be additionally filtered to remove organic contaminations. To maintain the water temperature, the water can pass through a heat exchanger 390.

Figure 13:
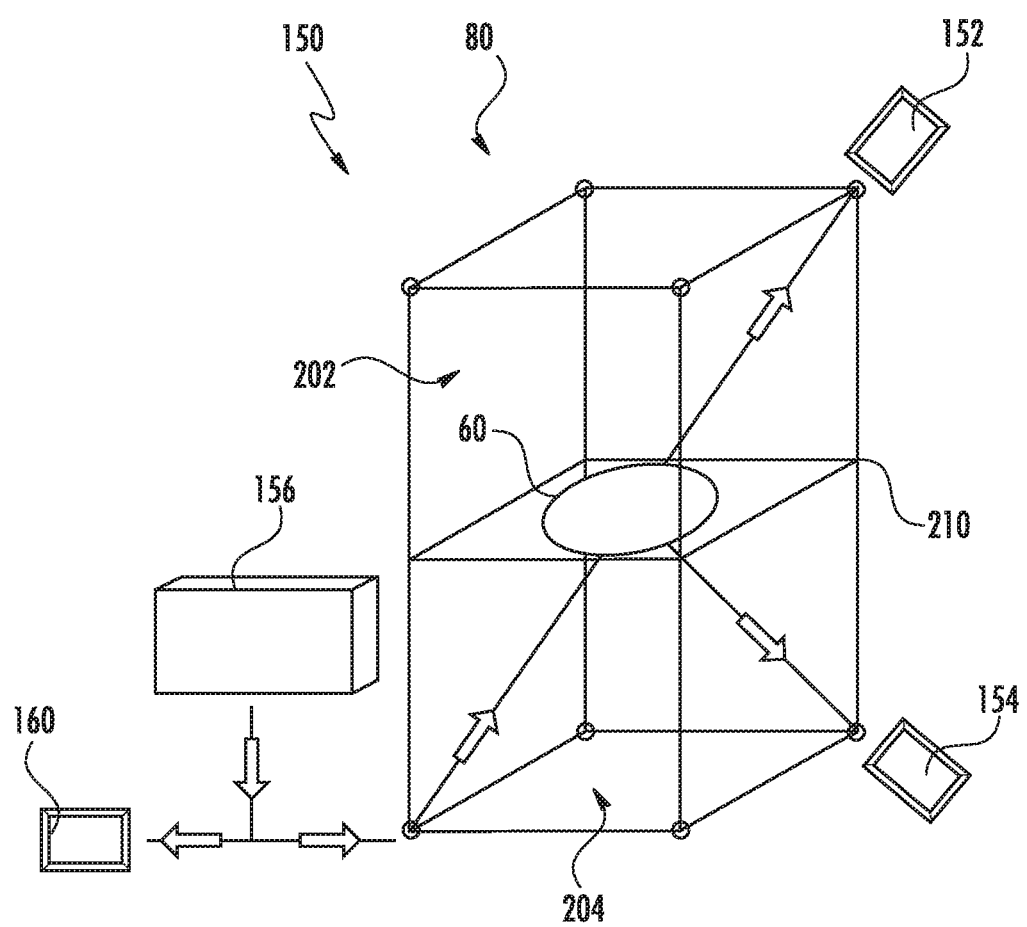
FIG. 13 depicts an example temperature measurement system for a millisecond anneal system according to example embodiments of the present disclosure.

Millisecond anneal systems according to example embodiments of the present disclosure can include the ability to independently measure temperature of both surfaces (e.g., the top and bottom surfaces) of the semiconductor substrate. FIG. 13 depicts an example temperature measurement system 150 for millisecond anneal system 200.

A simplified representation of the millisecond anneal system 200 is shown in FIG. 13. The temperature of both sides of a semiconductor substrate 60 can be measured independently by temperature sensors, such as temperature sensor 152 and temperature sensor 154. Temperature sensor 152 can measure a temperature of a top surface of the semiconductor substrate 60. Temperature sensor 154 can measure a bottom surface of the semiconductor substrate 60. In some embodiments, narrow band pyrometric sensors with a measurement wavelength of about 1400 nm can be used as temperature sensors 152 and/or 154 to measure the temperature of, for instance, a center region of the semiconductor substrate 60. In some embodiments, the temperature sensors 152 and 154 can be ultra-fast radiometers (UFR) that have a sampling rate that is high enough to resolve the millisecond temperature spike cause by the flash heating.

The readings of the temperature sensors 152 and 154 can be emissivity compensated. As shown in FIG. 13, the emissivity compensation scheme can include a diagnostic flash 156, a reference temperature sensor 158, and the temperature sensors 152 and 154 configured to measure the top and bottom surface of the semiconductor wafers. Diagnostic heating and measurements can be used with the diagnostic flash 156 (e.g., a test flash). Measurements from reference temperature sensor 158 can be used for emissivity compensation of temperature sensors 152 and 154

In some embodiments, the millisecond anneal system 200 can include water windows. The water windows can provide an optical filter that suppresses lamp radiation in the measurement band of the temperature sensors 152 and 154 so that the temperature sensors 152 and 154 only measure radiation from the semiconductor substrate.

The readings of the temperature sensors 152 and 154 can be provided to a processor circuit 160. The processor circuit 160 can be located within a housing of the millisecond anneal system 200, although alternatively, the processor circuit 160 may be located remotely from the millisecond anneal system 200. The various functions described herein may be performed by a single processor circuit if desired, or by other combinations of local and/or remote processor circuits.

Figure 16:
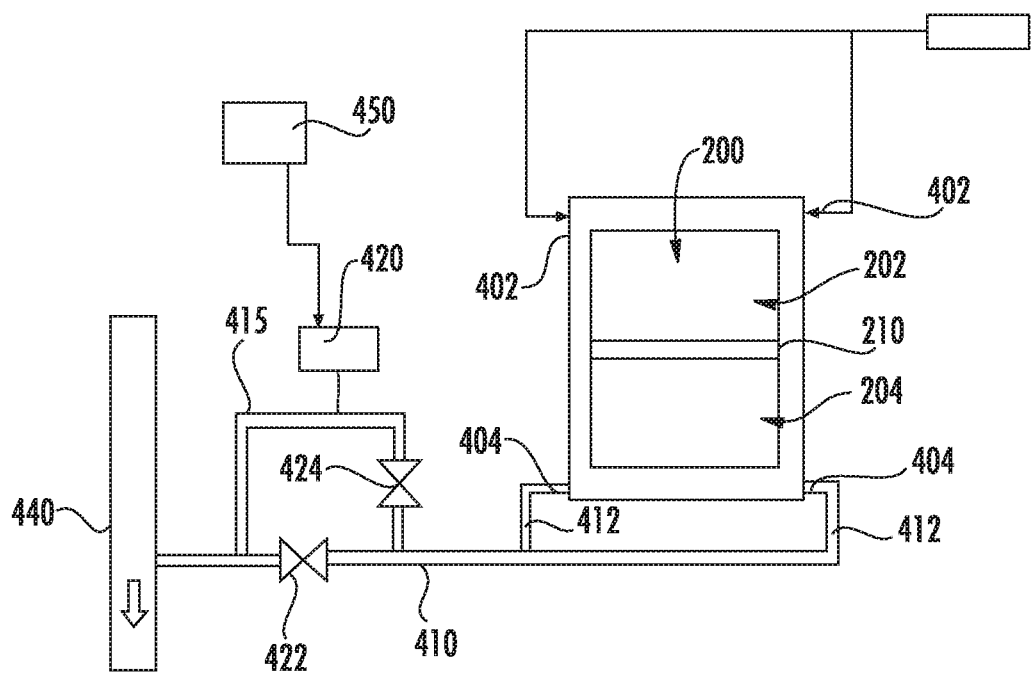
FIG. 16 depicts the example use of a vapor sensor in a gas flow system for fluid leakage detection according to example embodiments of the present disclosure.

As will be discussed in detail below, the temperature measurement system can include other temperature sensors, such as a temperature sensor configured to obtain one or more temperature measurements of a wafer support plate (e.g., as shown in FIG. 16) and/or a far infrared temperature sensor (e.g., as shown in FIG. 22) configured to obtain one or more temperature measurements of a semiconductor substrate at temperatures below, for instance, about 450° C. The processor circuit 160 can be configured to process measurements obtained from the temperature sensors to determine a temperature of the semiconductor substrate and/or the wafer support plate.

Figure 14:
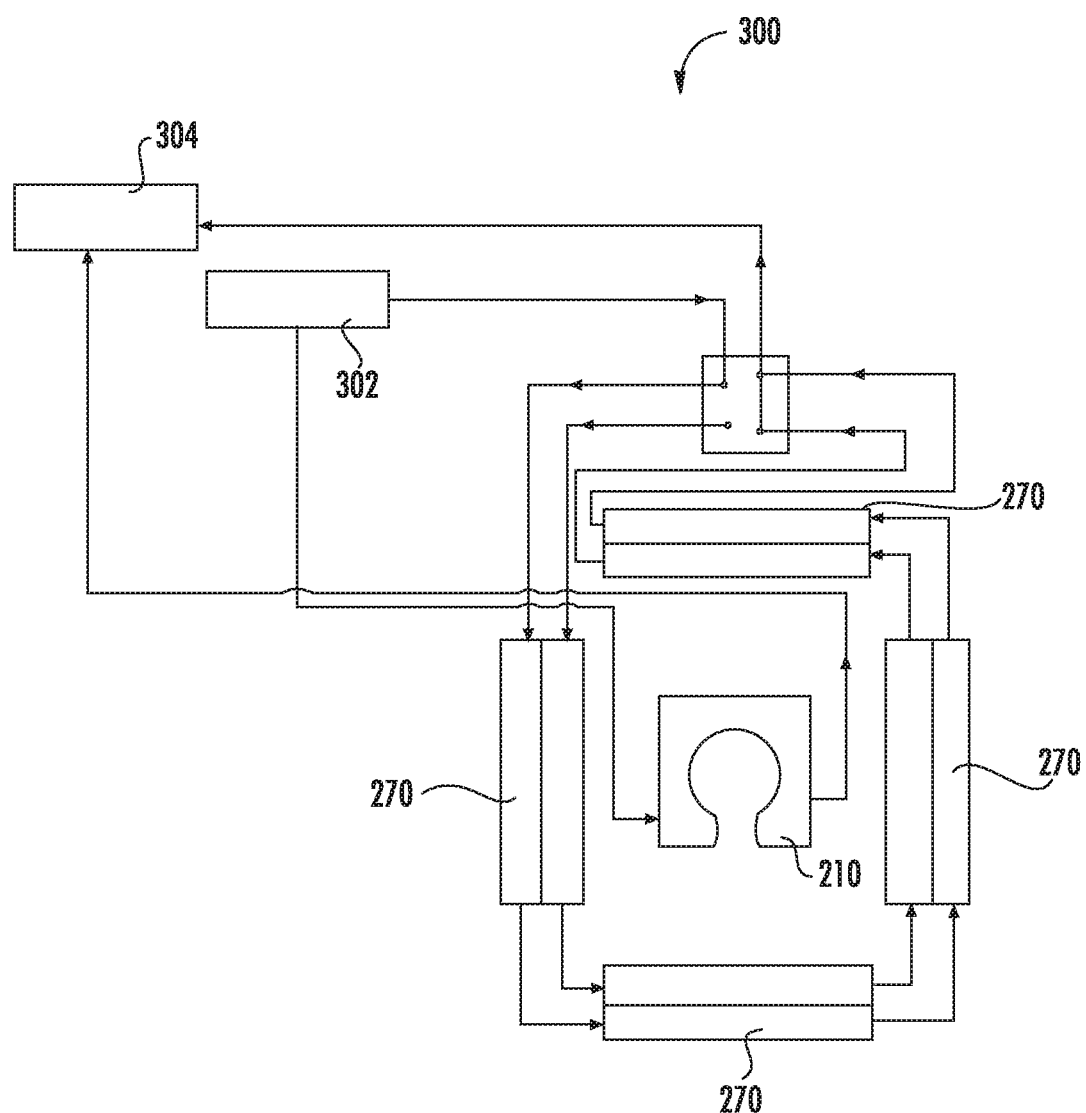
FIG. 14 depicts an example closed loop water circuit in a millisecond anneal system according to example embodiments of the present disclosure.

FIG. 14 depicts an example cooling system 300 for the reflective mirrors 270 and wafer plane plate 210 of an example millisecond anneal system according to example embodiments of the present disclosure. As shown the system can circulate a cooling fluid (e.g., water or other fluid) through the wafer plane plate 210 and the reflective mirrors 270 of a millisecond anneal system. The fluid can be sourced from a main fluid supply manifold 302. The fluid can be returned to a main fluid return manifold 304. The fluid can provide for temperature cooling of the wafer plane plate 210 and reflective mirrors 270 during thermal processing.

The millisecond anneal system can include other systems for circulating fluid (e.g., water) amongst the components of the millisecond anneal system. For instance, the millisecond anneal system can circulate a fluid (e.g., water) through the water windows 260 illustrated in, for instance FIG. 2.

Example Water Leakage Detection in a Millisecond Anneal System

According to example embodiments of the present disclosure, water or other fluid leaking into the process chamber from a cooling system (e.g., the cooling system 300 of FIG. 14) can be detected by a humidity sensor. More particularly, in some embodiments, a humidity sensor can be disposed in a gas flow system that can be configured to detect humidity in the gas vented from the process chamber. The presence of a leak can be detected by detecting levels of humidity that exceed a threshold humidity.

In some example embodiments, a humidity sensor can be placed downstream to the processing chamber in the main vent line for the gas flow system for a millisecond anneal system. The main vent line can combine the individual vent pipes from gas vents in the processing chamber.

Figure 15:
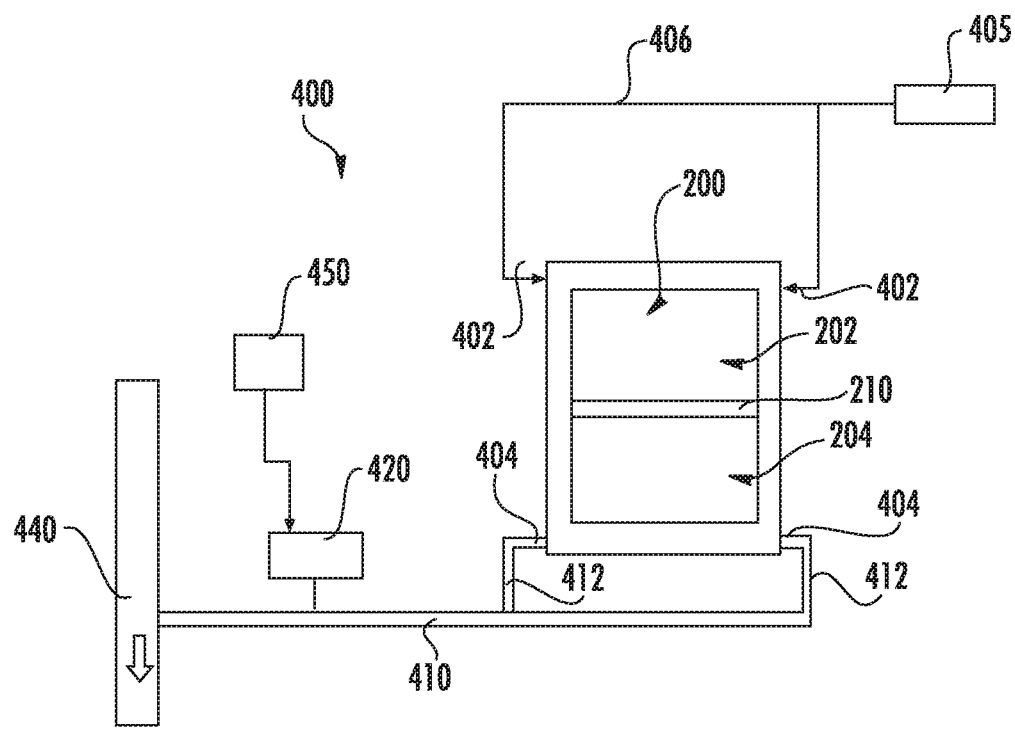
FIG. 15 depicts the example use of a vapor sensor (e.g., a humidity sensor) in a gas flow system for fluid leakage detection according to example embodiments of the present disclosure.

FIG. 15 depicts the example system for water leakage detection according to example embodiments of the present disclosure. As shown, a millisecond anneal system can include a gas flow system 400 for providing and exhausting process gas from process chamber 200. More particularly, a process gas (e.g., nitrogen, oxygen, ammonia, hydrogen, or forming gas, or mixtures thereof) can be provided to the processing chamber 200 from a gas source 405 through gas inlet 406. The gas inlet 406 can provide process gas to the process chamber 200 via vent openings 402 in the top chamber 202 (e.g., in the top corners of the top chamber 202 of the millisecond anneal system.

The gas flow system 400 can further include a gas outlet for exhausting gas from the process chamber 200. The gas outlet can include exhaust vent openings 404 in the bottom chamber 204 of the processing chamber 200 (e.g., the bottom corners of the processing chamber. Gas can be exhausted through the exhaust vent openings 404 into outlet lines 412, which can be coupled together at downstream line 410. The downstream line 410 can be exhausted to an external duct 440.

According to example aspects of the present disclosure, a humidity sensor 420 can be disposed in the downstream line 410. The humidity sensor 420 can be any sensor configured to detect an amount of humidity (e.g., moisture) in the gas flowing through downstream line 410. The humidity sensors 420 can send signals to a processor circuit 450. The processor circuit 450 can be configured to process the signals to determine whether a leak has occurred in a fluid cooling system of the millisecond anneal system.

In some embodiments, the processor circuit 450 can include one or more processors and one or more memory devices. The processor circuit 450 can be located within a housing of the millisecond anneal system, although alternatively, the processor circuit 450 may be located remotely from the millisecond anneal system. The various functions described herein may be performed by a single processor circuit if desired, or by other combinations of local and/or remote processor circuits. One example method executed by the processor circuit 450 will be discussed with reference to FIG. 17.

In this manner, the humidity sensor 420 can be sensitive to leaks independent of their location in the chamber. The humidity sensor 420 can be operated in a continuous reading mode at sample rates of, for example, 1 per minute or other suitable rate. The sensitivity of humidity measurement can selected such that the formation of leaks can be detected in real time and processing of semiconductor substrates with water or other fluid leaks can be reduced.

FIG. 16 depicts another example embodiment of the present disclosure. In this example embodiment, the humidity sensor is connected in parallel to the downstream line 410 by a by-pass line 415. In this manner, the sensor 420 can be disconnected from the downstream line 410 by electrically or pneumatically operated valves 422 and 424. This can be useful to prevent saturation of the sensor 420 when the chamber is opened to the humidity of the atmosphere (e.g., when a semiconductor substrate is loaded into the chamber). As a result, the latency until correct readings are available can be reduced.

Figure 17:
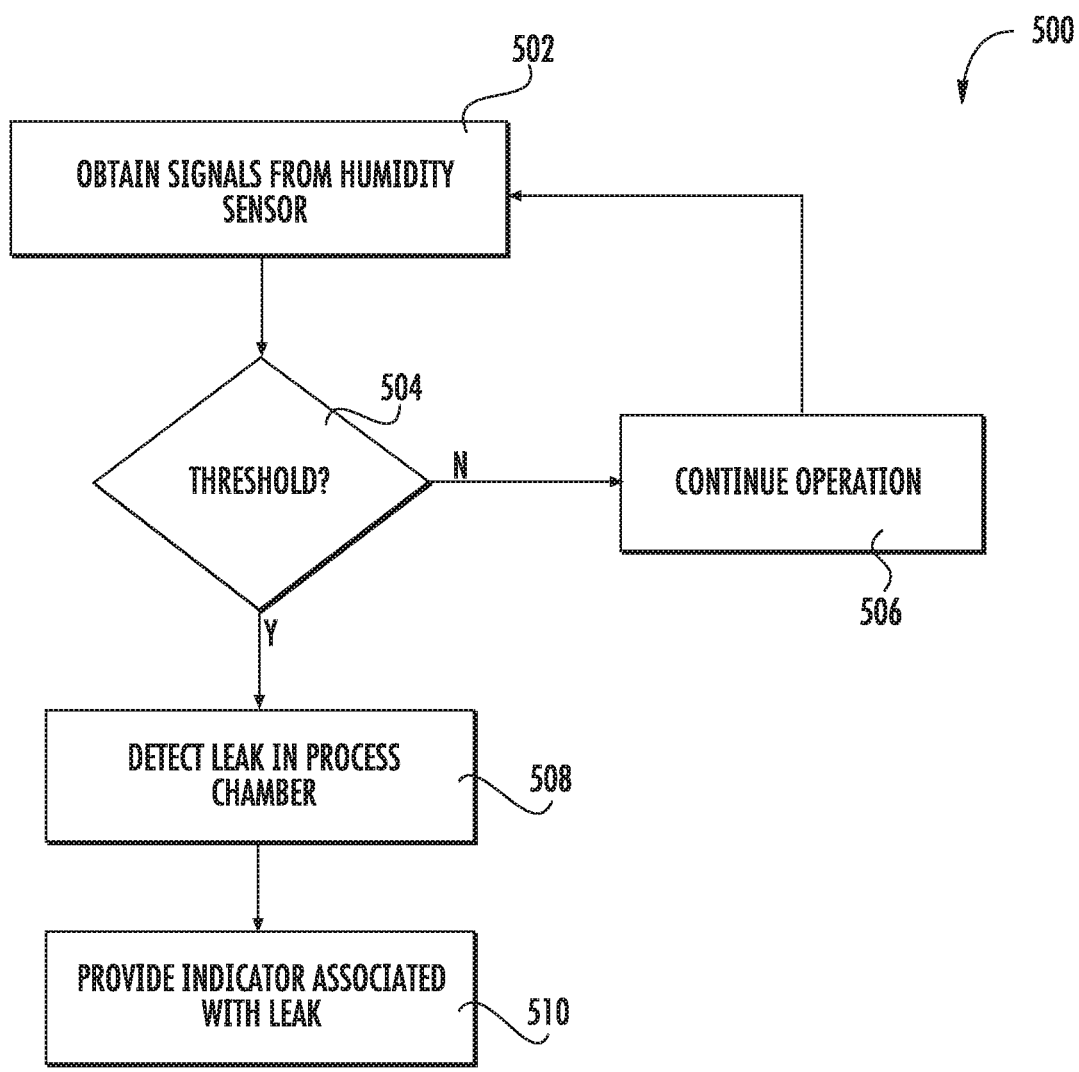
FIG. 17 depicts a flow diagram of an example method according to example embodiments of the present disclosure.

FIG. 17 depicts a flow diagram of an example method for detecting leaks in a millisecond anneal system according to example embodiments of the present disclosure. FIG. 17 can be implemented by one or more processor circuits, such as the processor circuit 450 of FIGS. 15 and 16. FIG. 17 depicts steps performed in a particular order for purposes of illustration and discussion. Those of ordinary skill in the art, using the disclosures provided herein, will understand that the various steps of any of the methods described herein can be adapted, modified, expanded, omitted, and/or rearranged in various ways without deviating from the scope of the present disclosure.

At (502), the method includes obtaining signals from a humidity sensor indicative of the humidity in a downstream line of a gas flow system in a millisecond anneal system. For instance, the method can include obtaining, by the processor circuit 450, signals from the sensor 420 in FIGS. 15 and 16.

At (504) of FIG. 16, the method can include processing the signals from the humidity sensor to determine whether the humidity in the downstream line exceeds a threshold humidity. The threshold humidity can be set to be indicative of a leak in the millisecond anneal system. If the humidity does not exceed the threshold, the method can continue operation of the millisecond anneal system as shown in FIG. 17.

However, when the humidity does exceed the threshold, the method can include detecting a leak in a fluid cooling system of the millisecond anneal system as shown at (508). The leak, for instance, can be in the cooling system for circulating fluid (e.g., water) through the reflective mirrors, water windows, wafer plane plate, or other fluid cooled components of the millisecond anneal system.

At (510), the method can include providing an indicator associated with the detected leak. The indicator can be any suitable notification or indication that a leak has occurred in the millisecond anneal system. For instance, the indicator can be an audio, visual, or other suitable indicator. In some embodiments, the indicator can be an electronic data notification communicated over a suitable communication medium (e.g., wired and/or wireless communication medium). In some embodiments, one or more control devices can automatically shut down operation of the millisecond anneal system based at least in part on the detected leak in the fluid cooling system.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A thermal processing system, comprising:
   a processing chamber comprising one or more fluid cooled components;
   a gas flow system configured to provide for a flow of process gas in the processing chamber and configured to exhaust the process gas from the processing chamber; and
   a humidity sensor configured to measure humidity in the process gas flowing downstream of an at least one exhaust vent opening configured to exhaust the process gas from the processing chamber in the gas flow system for detecting a fluid leak associated with the one or more fluid cooled components.

2. The thermal processing system of claim 1, wherein the processing chamber comprises a wafer plane plate dividing the processing chamber into a top chamber and a bottom chamber, the at least one exhaust vent opening being located in the bottom chamber.

3. The thermal processing system of claim 1, wherein the gas flow system comprises a downstream line coupled to the at least one exhaust vent opening.

4. The thermal processing system of claim 3, wherein the humidity sensor is configured to measure humidity in the process gas flowing in the downstream line.

5. The thermal processing system of claim 3, wherein the humidity sensor is configured to measure humidity in the process gas flowing in a bypass line coupled to the downstream line.

6. The thermal processing system of claim 5, wherein the gas flow system comprises a valve configured to control the flow of gas into the bypass line.

7. The thermal processing system of claim 1, wherein the system further comprises at least one processor circuit, the processor circuit configured to:
 obtain signals from the humidity sensor indicative of the humidity in the process gas flowing through the gas flow system; and
 detect the fluid leak associated with the one or more fluid cooled components based at least in part on the signals from the humidity sensor.

8. The thermal processing system of claim 7, wherein the processor circuit is configured to detect the fluid leak associated with the one or more fluid cooled components at least in part by comparing the amount of humidity in the process gas flowing through the gas flow system to a threshold and detecting the fluid leak when the amount of humidity in the process gas exceeds the threshold.

9. The thermal processing system of claim 7, wherein the processor circuit is configured to provide an indicator associated with the fluid leak.

10. The thermal processing system of claim 7, wherein the one or more fluid cooled components comprise a wafer plane plate.

11. The thermal processing system of claim 1, wherein the one or more fluid cooled components comprise a reflective mirror.

12. The thermal processing system of claim 1, wherein the one or more fluid cooled components comprise a water window.

13. A method for detecting a fluid leak in a millisecond anneal system, the method comprising:
 obtaining, by one or more processor circuits, one or more signals from a humidity sensor configured to measure humidity in process gas flowing downstream of an at least one exhaust vent opening configured to exhaust the process gas from a processing chamber in a gas flow system, the gas flow system configured to provide for the flow of the process gas in the processing chamber having one or more fluid cooled components, the gas flow system further configured to exhaust the process gas from the processing chamber; and
 detecting, by the one or more processor circuits, a fluid leak associated with the one or more fluid cooled components in the processing chamber based at least in part on the one or more signals from the humidity sensor.

14. The method of claim 13, wherein detecting, by the one or more processors circuits, a fluid leak associated with the one or more fluid cooled components in the processing chamber comprises:
 comparing, by the one or more processor circuits, the humidity in the process gas to a threshold; and
 detecting, by the one or more processor circuits, the fluid leak when the humidity in the process gas exceeds the threshold.

15. The method of claim 13, wherein the method further comprises providing, by the one or more processor circuits, an indicator associated with the fluid leak.

16. A millisecond anneal system, comprising:
 a processing chamber having a wafer plane plate dividing the processing chamber into a top chamber and a bottom chamber, the processing chamber having one or more reflective mirrors;
 a gas flow system configured to provide for the flow of process gas in the processing chamber, the gas flow system comprising at least one vent opening in the top chamber for providing the process gas to the processing chamber and at least one exhaust vent opening in the bottom chamber for exhausting the process gas from the processing chamber, the gas flow system further comprising a downstream line coupled to the at least one exhaust vent opening;
 a fluid cooling system configured to circulate fluid through one or more of the wafer plane plate and the one or more reflective mirrors; and
 a humidity sensor configured to measure humidity in the process gas flowing downstream of the at least one exhaust vent opening for detecting a leak associated with the fluid cooling system.

17. The millisecond anneal system of claim 16, wherein the system further comprises a processor circuit, the processor circuit configured to perform operations, the operations comprising:
 obtaining signals from the humidity sensor indicative of the humidity in the process gas flowing through the downstream line; and
 detecting the leak associated with the fluid cooling system based at least in part on the signals from the humidity sensor.

* * * * *